US008835386B2

(12) United States Patent (10) Patent No.: US 8,835,386 B2
Colgin et al. (45) Date of Patent: Sep. 16, 2014

(54) ACTIVITY OF RECOMBINANT EQUINE FOLLICLE STIMULATING HORMONE

(75) Inventors: Mark Colgin, Castle Rock, CO (US); Kory Niswender, Weatherford, TX (US); Irving Boime, St. Louis, MO (US); Janet Roser, Davis, CA (US)

(73) Assignees: Venaxis, Inc., Castle Rock, CO (US); Washington University, St. Louis, MO (US); The Regents of the University of California, Oakland, CA (US)

( * ) Notice: Subject to any disclaimer, the term of this patent is extended or adjusted under 35 U.S.C. 154(b) by 518 days.

(21) Appl. No.: 12/325,084

(22) Filed: Nov. 28, 2008
(Under 37 CFR 1.47)

(65) Prior Publication Data
US 2010/0120677 A1 May 13, 2010

Related U.S. Application Data

(60) Provisional application No. 60/991,297, filed on Nov. 30, 2007.

(51) Int. Cl.
*A61K 38/24* (2006.01)
*C07K 14/575* (2006.01)
*C07K 14/59* (2006.01)

(52) U.S. Cl.
USPC ............................ 514/9.9; 530/350; 530/398

(58) Field of Classification Search
None
See application file for complete search history.

(56) References Cited

U.S. PATENT DOCUMENTS

| | | | |
|---|---|---|---|
| 4,195,620 A | 4/1980 | Rust | |
| 4,440,150 A | 4/1984 | Kaehler | |
| 4,536,847 A | 8/1985 | Erickson et al. | |
| 4,780,451 A | 10/1988 | Donaldson | |
| 5,589,457 A | 12/1996 | Wiltbank et al. | |
| 5,792,785 A | 8/1998 | Sharp et al. | |
| 6,238,890 B1 * | 5/2001 | Boime et al. ................. | 435/69.7 |
| 6,242,580 B1 * | 6/2001 | Boime et al. ................. | 530/398 |
| 6,403,631 B1 | 6/2002 | Sharp et al. | |
| 6,455,282 B1 * | 9/2002 | Beck et al. ................... | 435/69.4 |
| 2002/0165146 A1 | 11/2002 | Hoffman et al. | |
| 2002/0165366 A1 * | 11/2002 | Musick et al. ............... | 530/399 |
| 2003/0092628 A1 | 5/2003 | deGreef et al. | |
| 2003/0144189 A1 | 7/2003 | Lustbader et al. | |
| 2003/0211580 A1 | 11/2003 | Lustbader | |
| 2005/0186662 A1 | 8/2005 | Low | |
| 2007/0197435 A1 | 8/2007 | Webel | |

FOREIGN PATENT DOCUMENTS

JP 11 147898 7/1999

OTHER PUBLICATIONS

Murphy et al., Endocrine reviews 12(1):27, 1991.*
Niswender et al., Journal of Equine Veterinary Science, 2003: 23: 497-500.*
Logan et al., Animal Reproduction Science, 2007; 102: 48-55.*
Binelli, M et al. "Antiluteolytic strategies to improve fertility in cattle"; (2001) *Theriogenology* 56:1451-1463.
Bousfield, GR et al. "Identification of twelve O-glycosylation sites in equine chorionic gonadotropin and equine luteinizing hormone β by solid-phase Edman degradation"; (2001) *J. Biol. Reprod.* 64:136-147.
Chagas E Silva et al. "Plasma progesterone profiles and factors affecting embryo-fetal mortality following embryo transfer in dairy cattle" ; (2002) *Theriogenology* 58(1):51-59.
De Rensis, F. et al. "Fertility in postpartum dairy cows in winter or summer following estruc synchronization and fixed time AI after the induction of an LH surge with GnRH or hCG"; (2000) *Theriogenology* 58(9):1675-1687.
D'Occhio, MJ et al. "Reproductive responses of cattle to GnRH agonists"; (2000) *Anim. Reprod. Sci.* 60-61:443-442.
Farin, CE . et al. "Effect of Luteinizing Hormone and Human Chorionic Gondadotropin on Cell Populations in the Ovine Corpus Luteum"; (1988) *Biol. Reprod.* 38:413-421.
Guillou, F et al. "Purification of equine gonadotropins and comparative study of their acid-dissociation and receptor-binding specificity" (1983) *Biochim. Biophys. Acta,* 755, 229-236.
Hoyer, PB et al. "The regulation of steroidogenesis is different in the two types of ovine luteal cells"; (1985) *Can. J. Physiol. Pharmacol.* 63(39):240-248.
Johnson, CA et al. "Pituitary responsiveness to GnRH in mares following deslorelin acetate implantation to hasten ovulation"; (2002) J. Anim. Sci. 80:2681-2687.
Juengel, JF et al. "The Development of Antibodies to Human Chorionic Gondadotrophin following its repeated injection in the cyclic mare"; (1999) *J. Reprod. Fertil. Suppl.* 54:193-205.
Lee, CN et al. "Efficacy of gonadotropin-releasing hormone administered at the time of artificial insemination of heifers and postpartum and repeat breeder dairy cows"; (1983) *Am. J. Vet. Res.* 44(11):2160-2163.
Lofstedt, RM "Control of the estrous cycle of the mare"; (1988) *The Veterinary Clinics of North America—Equine Practice*, 189-190.
Loy, RG et al. "Control of ovulation in cycling mares with ovarian steroids and prostaglandin"; (1981) *Theriogenology* 15:191-200.
Lucy, MC et al. "Reproductive endocrinology of lactating dairy cows selected for increased milk production"; (1998) *J. Anim. Sci.* 76(1);246.
Martinez, MF et al. "Effect of LH or GnRH on the dominant follicle of the first follicular wave in beef heifers"; (1999) *Anim. Reprod. Sci* 57:23-33.
Moore, WT et al. "Pregnant mare serum gonadotropin. An in vitro biological characterization of the lutropin-follitropin dual activity"; (1980) *J. Biol. Chem.* 255:6923-6929.

(Continued)

*Primary Examiner* — Christina Borgeest
(74) *Attorney, Agent, or Firm* — Lathrop & Gage LLP

(57) ABSTRACT

The present invention provides methods of producing biologically active recombinant eFSH analogs and methods of increasing reproduction in mammals, particularly equine, using recombinant eFSH analogs. Also provided are methods of producing biologically active single chain recombinant eFSH. The recombinant eFSH analogs of the present invention increase superovulation, follicular development, embryo development, and reproductive efficiency in horses, cattle and other ungulates.

7 Claims, 5 Drawing Sheets

(56) References Cited

OTHER PUBLICATIONS

Narayan, P et al. "Functional expression of yoked human chorionic gonadotropin in baculovirus-infected insect cells"; (1995) *Mol. Enocrinol.* 9:1720-1726.

Pierce, JG et al. "Glycoprotein hormones: structure and function"; (1981) *Biochem.* 50:465-495.

Roser, JF et al. "The development of antibodies to human chorionic gonadotropin following its repeated injections in the cyclic mare," (1979) *J. Reprod. Fertil.* 27: 173-179.

Sangsritavong, S et al. "Liver blood flow and steroid metabolism are increased by both acute feeding and hypertrophy of the digestive tract"; (2000) *J. anim. Sci.* 78(1):221.

Santos, JEP et al. "Effect of human chorionic gonadotropin on luteal function and reproductive performance of high-producing lactating Holstein dairy cows"; (2001) *J. animal Sci.* 79-2881-2894.

Scoggin, CF et al. "Strategies to improve the ovarian response to equine pituitary extract in cyclic mares," (2002) Theriogenology. 58(1):151-64.

Sugahara, T et al. "Biosynthesis of a biologically active single peptide chain containing the human α and chorionic gondadotropin β subunits in tandem"; (1995) *Proc. Natl. Acad. Sci. USA* 92:2041-2045.

Thatcher, WW et al. "Effects of hormonal treatments on reproductive performance and embryo production" (2001) *Theriogenology* 55:75-89.

Varner, DD et al. "Estrogens, oxytocin and ergot alkaloids—Uses in reproductive management of mares"; (1988) *Proc. Am. Assoc. Equine Pract.* 219-241.

Vasconcelos, JLM et al "Reduction in size of the ovulatory follicle reduces subsequent luteal size and pregnancy rate"; (2001) *Theriogenology* 56:307-314.

Weems, YS et al. "Effect of Luteinizing Hormone (LH), $PGE_2$, 8-EPI-$PGE_1$, 8-EPI-$PGE_2$, Trichosanthin, and Pregnancy Specific Protein B (PSPB) on Secretion of Progesterone In Vitro by Corpora Lutea CL) from Nonpregnant and Pregnant Cows"; (1998) *Prostaglandins and other Lipid Mediators* 55:27-42.

Wiltbank, MC et al. "Novel effects of nutrition on reproduction in lactating dairy cows"; (2001) *J. Dairy Sci.* 84(1):84.

Deluca, C.A. et al. "Comparison of three doses of reFSH for superovulation of mares"; (2008) *Theriogenology* 70(3):587-588.

Saneyoshi et al. "Equine follicle-stimulating hormone: molecular cloning of beta-subunit and biological role of the asparagine-linked oligosaccharide at asparagine of alpha-subunit"; (2001) *Biol.Reprod.* 65:1686-1690.

EP supplemental Search Report 08856937.1.

International Search Report PCT/US 08/85072.

Furuhashi et al. "Fusing the Carboxy-Terminal Peptide of the Chorionic Gonadotropin (CG) 13-Subunit to the Common a-Subunit: Retention of O-Linked Glycosylation and Enhanced in Vivo Bioactivity of Chimeric Human CG"; (1995) *Mol. Endocrinology,* 9(1):54-63.

European Office Action for EP 08 856 937.1, Jul. 24, 2013.

\* cited by examiner

```
atgaagtcagtccagttttgtttccttttctgttgctggaaagcagtctgctgcaatagc
 M  K  S  V  Q  F  C  F  L  F  C  C  W  K  A  V  C  C  N  S
tgtgagctgaccaacatnaccatcgccgtggagaaggaggaatgtggcttctgcataagc
 C  E  L  T  N  T  T  I  A  V  E  K  E  E  C  G  F  C  I  S
atcaacaccacctggtgtgcgggctactgctacacccgggacctggtgtacaaggaccca
 I  N  T  T  W  C  A  G  Y  C  Y  T  R  D  L  V  Y  K  D  P
gcccggcccaacatccagaaaacatgcaccttcaaggagctggtgtacgagacagtgaaa
 A  R  P  N  I  Q  K  T  C  T  F  K  E  L  V  Y  E  T  V  K
gtgcctggctgtgctcaccacgcggactccctgtacacgtacccggtggccactgcatgt
 V  P  G  C  A  H  H  A  D  S  L  Y  T  Y  P  V  A  T  A  C
cactgtggcaaatgtaacagcgacagcactgactgcaccgtgcgaggtctggggcccagc
 H  C  G  K  C  N  S  D  S  T  D  C  T  V  R  G  L  G  P  S
tactgctccttcggtgacatgaaggaatcctcttcctctaaggatcccccatcccaacct
 Y  C  S  F  G  D  M  K  E  S  S  S  S  K  D  P  P  S  Q  P
ctcacatccacatccaccccaactcctggggccagcagacgttcctctcaccccctccca
 L  T  S  T  S  P  T  P  G  A  S  R  R  S  S  H  P  L  P
ataaagacttcttttcctgatggagagtttacaacgcaagactgtcctgaatgcaagcta
 I  K  T  S  F  P  D  G  E  F  T  T  Q  D  C  P  E  C  K  L
agggaaaacaagtacttcttcaaactgggcgtcccgatttaccagtgtaagggctgctgc
 R  E  N  K  Y  F  F  K  L  G  V  P  I  Y  Q  C  K  G  C  C
ttctccagagcgtaccccactccagcaaggtccaggaagacaatgttggtcccaaagaac
 F  S  R  A  Y  P  T  P  A  R  S  R  K  T  M  L  V  P  K  N
atcacctcagaatccacatgctgtgtggccaaagcatttatcagggtcacagtgatggga
 I  T  S  E  S  T  C  C  V  A  K  A  F  I  R  V  T  V  M  G
aacatcaagttggagaaccacacccagtgctattgcagcacttgctatcaccacaagatt
 N  I  K  L  E  N  H  T  Q  C  Y  C  S  T  C  Y  H  H  K  I
taa
 *
```

FIGURE 1

ACTIVITY OF RECOMBINANT EQUINE FOLLICLE STIMULATING HORMONE

CROSS-REFERENCE TO RELATED APPLICATIONS

This application claims the benefit of U.S. Provisional Application 60/991,297, filed Nov. 30, 2007, which is hereby incorporated by reference in its entirety to the extent not inconsistent with the disclosure herein.

BACKGROUND OF THE INVENTION

Progesterone is required to maintain pregnancy and low progesterone concentrations are associated with infertility. Blood progesterone concentrations are influenced by rates of secretion and metabolism/clearance. There is evidence that modern dairy cows maintain lower blood progesterone concentrations than those measured in cattle several decades ago (Lucy et al. (1998) "Reproductive endocrinology of lactating dairy cows selected for increased milk production," J. Anim. Sci., 76 (Suppl. 1):296). Larger corpora lutea secrete more progesterone and have a positive effect on pregnancy recognition and pregnancy rates, but there is evidence that dairy cows have smaller than desirable corpora lutea in some circumstances (Lucy 2001, supra; Vasconcelos et al. (2001) "Reduction in size of the ovulatory follicle reduces subsequent luteal size and pregnancy rate," Theriogenology, 56:307-314). The liver is the primary site of progesterone metabolism. Recent studies show that increased feed intake increases liver blood flow and increases the rate of progesterone clearance, thus decreasing serum progesterone concentrations (Sangsritavong et al. (2000) "Liver blood flow and steroid metabolism are increased by both acute feeding and hypertrophy of the digestive tract," J. Anim. Sci., 78 (Suppl 1)221; and Wiltbank, M. C. et al. (2001) "Novel effects of nutrition on reproduction in lactating dairy cows," J. Dairy Sci., 84 (Suppl. 1):84).

Low serum progesterone during the luteal phase of the estrus cycle would be associated with low first service conception rate. Low progesterone concentrations may result from inadequate secretion, or alternatively high levels of metabolism/clearance, even when insemination has produced a potentially viable embryo. Low progesterone would allow the generation of prostaglandin by uterine endometrium at around day 16 of the bovine estrus cycle, resulting in luteolysis and induction of ovulation, thus embryonic death and failure to maintain the pregnancy (Binelli, M. et al. (2001) "Antiluteolytic strategies to improve fertility in cattle," Theriogenology, 56:1451-1463). Increasing serum progesterone or maintaining the proper levels of serum progesterone in fertilized animals is a promising therapeutic method for maintaining pregnancy and preventing pregnancy loss.

Currently, several hormone therapies are used to increase fertility or to maintain pregnancy. Thatcher et al. (2001 Theriogenology 55:75-89) describes the effects of hormonal treatments on the reproductive performance of cattle. Hormonal treatments include administration of bovine somatotrophin (bST) and human chorionic gonadotropin (hCG). D'Occhio et al. (2000 Anim. Reprod. Sci. 60-61:433-442) describes various strategies for beef cattle management using gonadotropin releasing hormone (GnRH) agonist implants. De Rensis et al. (2002 Theriogenology 58(9):1675-1687) describes the effect on dairy cows of administering GnRH or hCG before artificial insemination. Martinez et al. (1999 Anim. Reprod. Sci. 57:23-33) describes the ability of porcine luteinizing hormone (LH) and GnRH to induce follicular wave emergence in beef heifers on Days 3, 6, and 9 of the estrus cycle, after ovulation (Day 0), without insemination. Santos et al. (2001 J. Animal Science 79:2881-2894) describes the effect on reproductive performance of intramuscular administration of 3,300 IU of hCG to high-producing dairy cows on Day 5 after artificial insemination. Lee et al. (1983 Am. J. Vet. Res. 44(11):2160-2163) describes the effect on dairy cows of administering GnRH at the time of artificial insemination. U.S. Pat. Nos. 5,792,785 (issued Aug. 11, 1998) and 6,403,631 (issued Jun. 11, 2002) describe methods and compositions for administering melatonin before and after insemination to enhance pregnancy success in an animal. Chagas e Silva et al. (2002 Theriogenology 58(1):51-59) describes plasma progesterone profiles following embryo transfer in dairy cattle. Weems et al. (1998 Prostaglandins and other Lipid Mediators) describes the effects of hormones on the secretion of progesterone by corpora lutea (CL) from non-pregnant and pregnant cows. U.S. Pat. No. 4,780,451 (issued Oct. 25, 1988) describes compositions and methods using LH and follicle stimulating hormone to produce superovulation in cattle; Farin et al. (1988 Biol. Reprod. 38:413-421) describes the effect on ovine luteal weight of intravenous administration of 300 IU of hCG on Days 5 and 7.5 of the estrus cycle, without insemination. Hoyer and Niswender (1985 Can. J. Physiol. Pharmacol. 63(3):240-248) describe the regulation of steroidogenesis in ovine luteal cells. Juengel and Niswender (1999 J. Reprod. Fertil. Suppl. 54:193-205) describe the molecular regulation of luteal progesterone in domestic ruminants. U.S. Pat. No. 5,589,457 (issued Dec. 31, 1996) describes methods for synchronizing ovulation in cattle using GnRH, LH, and/or hCG and PGF2α.

Many of these treatments use hormones or hormone analogs from the glycoprotein hormone family, which consists of the pituitary proteins luteinizing hormone (LH), follicle-stimulating hormone (FSH), thyroid stimulating hormone (TSH) and chorionic gonadotropin (CG). The gonadotropins, which include CG, FSH and LH, are essential for reproductive function. They are heterodimers composed of two non-covalently associated α and β subunits. Both subunits are glycosylated, containing asparagine (N)-linked oligosaccharides and, in the case of the CGβ subunit, O-linked carbohydrates are also present in a cluster of amino acids at the C-terminus. The individual human β subunits are encoded by separate genes, and the LHβ and CGβ proteins are structurally and functionally similar; having more than 80% amino acid identity (Pierce J G, Parsons (1981) "Glycoprotein hormones: structure and function," Biochem. 50:465-495). Within a species, the α subunit amino acid sequence is common to all four hormones (Pierce J G, Parsons (1981) Biochem. 50:465-495).

All mammals synthesize LH, but CG has only been identified in primates and equids. In contrast to the primates, the equine LHβ and equine CGβ proteins are encoded by the same gene and have the same protein sequence. However, the N-linked oligosaccharides in placental equine CG (eCG) contain terminal galactose and sialic acid, while GalNAc sulfate is the primary terminal residue in pituitary equine LH (eLH). The carbohydrate content of eCG exceeds 40% of its mass and is the most glycosylated of the entire species of glycoprotein hormones (Bousfield et al. (2001) "Identification of twelve O-glycosylation sites in equine chorionic gonadotropin and equine luteinizing hormone β by solid-phase Edman degradation," Biol Reprod. 64:136-147; Moore and Ward (1980) "Pregnant mare serum gonadotropin. An in vitro biological characterization of the lutropin-follitropin dual activity," J Biol Chem 255: 6923-6929). This is attributed to a greater abundance of O-linked carbohydrate units compared with the primate CG. By contrast, the carbohydrate content of eLH is 25% (Bousfield et al. (2001) Biol Reprod. 64:136-147).

In the mare and stallion, use of a variety of hormones from other species is unsatisfactory due to their potential in eliciting a strong immune response. One such hormone that induces an antibody response is hCG (Roser et al., 1979). As alternatives, GnRH, equine pituitary extracts and equine chorionic gonadotropin (eCG; formally called pregnant mare serum gonadotropin (PMSG)) have been tried. Short acting Buserelin (a GnRH agonist) has been successful in inducing ovulation but requires more than one injection to induce ovulation within a 48 hour period. Cystorelin (native GnRH) is also short acting requiring more than one injection and is not licensed for use in the horse. Deslorelin (a GnRH analog) works very well in stimulating ovulation within 24-48 hours. Deslorelin has been on the market in two forms; a slow release implant or a slow release injectable. The implant, Ovuplant™, was found to be effective in inducing ovulation within 48 hours but in some mares prevented them from coming back into heat for several weeks when applied as directed (Johnson et al., 2002). Ovuplant™ is currently off the market. The injectable form of GnRH works well and is somewhat available as a "compounding reagent".

Pituitary extracts can be effective reproductive therapeutics but contain contaminants and may vary in their amounts of LH and FSH. Treatment with pituitary extracts or GnRH to a mare or stallion results in exposure of the gonads to a relatively fixed ratio of LH and FSH, offering limited possibilities of manipulating the gonads for follicular development, ovulation or spermatogenesis. In addition equine pituitary extracts contain only 8-10% LH and 6-8% FSH (Guillou and Combarnous, 1983), requiring the use of large treatment doses to be effective. Equine pituitary extracts appears to increase the number of follicles for ovulation, but the number of ovulations and number of embryos obtained do not appear to always correlate with the number of follicles developed (Scoggins et al., 2002). Equine CG has been shown to have little, if any, effect in the mare to stimulate follicular development and ovulation during estrus probably due to its inability to bind to ovarian tissue during estrus (Stewart and Allen, 1979).

In order to use equine gonadotropins to improve reproduction efficiency in equines and other species, the availability of purified proteins is essential. Currently, the sources for equine gonadotropins are serum (eCG-PMSG) and whole pituitary extracts. To obtain sufficient quantities of these native hormones for such work is expensive and difficult. Preparations of pure pituitary equine gonadotropins without cross-contamination are not readily available. Given the problem of animal-to-animal variation of native equine gonadotropins and the charge heterogeneity in the N-linked carbohydrates, the ability to generate the corresponding recombinant proteins will yield gonadotropins of a more homogeneous composition that can be standardized with respect to mass and bioactivity. Such proteins will be critical for calibrating clinical laboratory assays and for breeding management, such as shortening the time to ovulation in transitional and cycling mares for natural breeding and artificial insemination. The use of recombinant forms, as opposed to hormones extracted from serum and pituitary tissue, would avoid the co-contamination of pathogens and agents with a propensity to cause prion related diseases.

There is a need in the art for improved safe therapeutics for increasing the efficiency of breeding in horses and cattle, primarily by increasing ovulation, and then by maintaining pregnancy of post-inseminated mares and cows.

SUMMARY OF THE INVENTION

The present invention provides a follicle stimulating hormone (FSH) analog, particularly a recombinant equine FSH analog, and methods of using such analogs to improve the reproductive efficiency of horses, cattle and other mammals. Recombinant equine FSH (recombinant eFSH or reFSH) can improve reproduction, not only in horses, but in other species as well, by promoting superovulation, follicular development and embryo production. Using a reFSH analog to stimulate follicular development and/or superovulation offers the advantage of using a pure FSH product without the protein contaminants or unwanted LH activity of equine pituitary extract. The present invention also provides a reliable method of producing biologically active reFSH. Preferably the subunits of the recombinant FSH analog are linked together to form a single chain FSH analog.

In one embodiment, the present invention provides a method of stimulating follicular development or superovulation in mammals, preferably ungulates such as horses or cattle, comprising administering an effective dose of recombinant eFSH to the animal. In a further embodiment, the recombinant eFSH is administered in multiple intramuscular injections. Preferably, the recombinant eFSH is a single chain recombinant eFSH. In one embodiment, the present invention provides a single chain recombinant eFSH analog comprising an eFSH beta subunit connected to an equine CTP linker sequence connected to an eFSH alpha subunit. The amino acid and nucleotide sequence for one such eFSH analog (FSHβCTPα) is shown in FIG. 1. A cell-based bioassay has been established, and an ELISA has been developed for this analog. Furthermore, both amplified and scaled expression has been achieved.

The present invention provides bioactive compositions and methods of using such compositions including active eFSH analogs, particularly single chain recombinant eFSH analogs. Such active recombinant eFSH analog products are beneficial for improving reproduction activity, superovulation, follicular development and embryo production in equine and other mammalian species. Recombinant eFSH analogs also avoid cross contamination issues and do not elicit a strong immune response in treated animals.

In one embodiment, eFSH analogs are used to increase reproductive activity in ungulates, specifically horses and cattle. In particular, a single chain recombinant eFSH analog is used to stimulate superovulation, increase embryo production, and increase reproduction in female animals. Administering eFSH in order to increase reproduction, increase the number of produced embryos, or induce superovulation is desirable in a number of species including, but not limited to bovine, sheep, goats, cervids, yaks, water buffaloes, bison, antelopes, gazelles, elk, reindeer, moose, bighorn sheep, giraffes, and camelids including bactrian and dromedary camels, llamas, swine, equine, alpacas, and vicunas. This method is particularly effective for increasing superovulation, follicular development, embryo production, and pregnancies in equine and bovine. The eFSH analogs used in embodiments of the present invention are at least 95% pure and are preferably recombinant polypeptides. More preferably, the eFSH analog is a biologically active single chain recombinant eFSH.

One embodiment of the invention provides a method of making recombinant eFSH analogs by expressing DNA encoding eFSH alpha and beta subunits. In one embodiment, a single chain recombinant eFSH analog is produced where the alpha subunit is covalently linked to the beta subunit using a linker peptide. Native FSH is produced as separate alpha and beta subunits which non-covalently assemble together within the body of the animal. The single chain recombinant eFSH of the present invention has a high level of expression and bioactivity and is believed to have increased in vivo efficacy and duration compared to native eFSH because the alpha and beta subunits do not have to first assemble together and do not freely dissociate from each other. In one embodiment, a recombinant eFSH analog (named herein as FSH-βCTPα) is a single chain recombinant eFSH analog where the alpha and beta subunits from equine FSH are linked together using an equine chorionic gonadotropin carboxy terminal peptide.

The amino acid sequences of the eFSH alpha and beta subunits used herein are given in SEQ ID NO 5 and SEQ ID NO 6, respectively. DNA sequences encoding these amino acid sequences are given in SEQ ID NO 1 and SEQ ID NO 2, respectively, although additional DNA sequences may encode the same alpha and beta subunits due to the redundancy of the genetic code. It is understood that an eFSH analog may have minor differences in the amino acid sequence compared to the provided eFSH sequences without affecting function. Additionally, an eFSH analog may have additional or deleted amino acids compared to the provided eFSH sequences without affecting function. Preferably, the eFSH analog contains additions or deletions of 25 or fewer amino acids, more preferably 10 or fewer amino acids, or more preferably 5 or fewer amino acids, than the eFSH sequences provided in SEQ ID NO 5 and SEQ ID NO 6.

In one embodiment, the single chain eFSH analog has alpha and beta subunits that are at least 80% identical in sequence to the equine FSH alpha and beta subunits of SEQ ID NO 5 and SEQ ID NO 6. Preferably the eFSH analog comprises a first polypeptide having at least 85% homology with SEQ ID NO 5 and a second polypeptide having at least 85% homology with SEQ ID NO 6. More preferably, the first polypeptide has at least 90% homology with SEQ ID NO 5 and the second polypeptide has at least 90% homology with SEQ ID NO 6. Even more preferably, the first polypeptide has at least 95% homology with SEQ ID NO 5 and the second polypeptide has at least 95% homology with SEQ ID NO 6.

Preferably, the eFSH analog is a single chain polypeptide where a first polypeptide corresponding to the alpha subunit and a second polypeptide corresponding to the beta subunit are covalently linked. By covalently linked, it is meant that the first polypeptide is attached to the second polypeptide directly or through a linker peptide, where one end of the linker peptide is attached to the first polypeptide and the other end of the linker peptide is attached to the second polypeptide. Linker peptides able to attach to polypeptides in recombinant protein synthesis are well known in the art, and any linker peptide suitable to be expressed as part of the eFSH analog may be used. Preferably, the linker peptide has between approximately 10 and 50 amino acids, more preferably between approximately 20 and 40 amino acids. In one embodiment, the linker sequence is a human CTP linker sequence or a linker sequence having at least 90% sequence homology to the equine CTP linker. In a further embodiment, the peptide linker is equine chorionic gonadotropin carboxy terminal peptide (CTP). It should be understood that the positions of the alpha and beta subunit are reversible, in that the eFSH analog may have the configuration (alpha subunit)-linker-(beta subunit) or (beta subunit)-linker-(alpha subunit). In one embodiment, the nucleic acid molecules coding for the eFSH analog are incorporated into an expression vector which is transfected into a cell or cell line able to express the vector.

In one embodiment, an eFSH analog is used to produce a superovulation event that results in the recovery of viable embryos. In another embodiment, an eFSH analog is used to increase follicular development or embryo production. Inducing superovulation and increasing embryo production are useful for embryo transplantation and in vitro fertilization. In one embodiment, an effective amount of an eFSH analog is administered to one or more ungulates, preferably equine or bovine, in order to increase reproduction. In the present invention, the single chain recombinant eFSH may be administered to the animals as a single dose or multiple doses over several days for each estrus cycle. In one embodiment, the recombinant eFSH is administered daily for approximately 2 to 10 days, preferably for approximately 4 to 9 days, more preferably for approximately 5 to 8 days. A single dose of the recombinant eFSH may be administered per day to the animal, or two or more doses may be administered per day, for example at 6 hour, 8 hour or 12 hour intervals. In one embodiment, a single daily dose is administered or alternatively multiple daily doses are administered to the animal but in smaller amounts than in comparable FSH analog treatments. This can be attributed to increased activity and longer duration by the single chain FSH analog.

In one embodiment, the eFSH analog is administered to the animal approximately 6 to 16 days following ovulation, preferably between about day 8 and about day 14 after ovulation. The eFSH analog can be administered as a single intramuscular injection on each day or in multiple injections each day. The animals are checked for signs of heat and then bred by natural or artificial insemination. In a further embodiment, insemination occurs approximately 2 to 8 days, preferably 4 to 6 days, after the final administration of the eFSH. In another further embodiment, the embryos are flushed approximately 6-8 days after heat for subsequent use.

Additional hormones, such as luteinizing hormone, chorionic gonadotropin and prostaglandin, are optionally administered as well as the eFSH analog. In one embodiment, prostaglandin is administered to the animal in addition to administration of the recombinant eFSH analog. The prostaglandin is optionally administered as a single dose, typically by injection, or as multiple doses administered several hours apart. In one embodiment, a first dose of prostaglandin is given to the animal after administration of the eFSH analog followed by a second dose of prostaglandin which is given to the animal approximately 6 hours to 1 day following the first prostaglandin dose.

In one embodiment, each dose of the eFSH analog administered to the animal is between about 0.01 µg and about 5 mg. Preferably between about 1.0 µg and about 0.2 mg of the eFSH analog is administered to the animal, more preferably between about 200 µg and about 0.1 mg, even more preferably between about 500 µg and about 850 µg. The eFSH analog can be administered using any means known in the art, including but not limited to intramuscular injection and intravenous injection. Preferably the eFSH analog is administered through intramuscular injection.

Another embodiment provides a kit for inducing superovulation, follicular development, or increasing the number of embryos in a single estrus cycle in a mammal such as an equine or bovine comprising: at least one dose comprising an effective amount of single chain recombinant eFSH analog comprising a first polypeptide having at least 95% homology with SEQ ID NO 5, and a second polypeptide having at least 95% homology with SEQ ID NO 6, wherein the first and second polypeptides are covalently linked; a device for administering a dose of the eFSH analog; and instructions for administering the dose of the eFSH analog. In a further embodiment, the kit comprises two or more doses comprising an effective amount of a single chain recombinant eFSH. In one embodiment, the effective amount of the eFSH analog in each dose is between about 1 μg and about 0.2 mg, more preferably between about 200 μg and about 0.1 mg, even more preferably between about 500 μg and about 850 μg, and can vary depending on the kit. The device for administering the dose to the animal can be any device known in the art, such as needles and syringes. Optionally, the device is an injection device suitable for delivering a single dose of the eFSH analog. The kit may also comprise components such as additional hormones, such as prostaglandin, and injection devices for administering additional hormones.

In one embodiment, a composition of the invention comprises a protein composition as described herein, such as an eFSH composition, in a pharmaceutical formulation. In a further embodiment, the invention provides a method of synthesizing a composition of the invention or a pharmaceutical formulation thereof. A pharmaceutical formulation comprises one or more excipients, carriers, and/or other components as is understood in the art. Preferably, the components meet the standards of the National Formulary ("NF"), United States Pharmacopoeia ("USP"), or Handbook of Pharmaceutical Manufacturing Formulations. In an embodiment, an effective amount of a composition of the invention can be a therapeutically effective amount. In an embodiment, the invention provides a method for treating a medical condition comprising administering to a subject in need thereof, a therapeutically effective amount of a composition of the invention. In an embodiment, the invention provides a medicament which comprises a therapeutically effective amount of one or more compositions of the invention. In an embodiment, the invention provides a method for making a medicament for a purpose or treatment of a condition described herein.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

BRIEF DESCRIPTION OF THE DRAWINGS

FIG. 1 shows the amino acid (SEQ ID NO: 8) and DNA sequence (SEQ ID NO: 4) of a single chain recombinant eFSH analog (FSHβCTPα) of the present invention where the beta subunit and alpha subunit are covalently linked together using an equine CTP (underlined).

As shown in FIG. 4, the single chain recombinant eFSH analog has approximately equal or greater biological activity than the native eFSH, especially at lower doses.

DETAILED DESCRIPTION OF THE INVENTION

Figure 2:
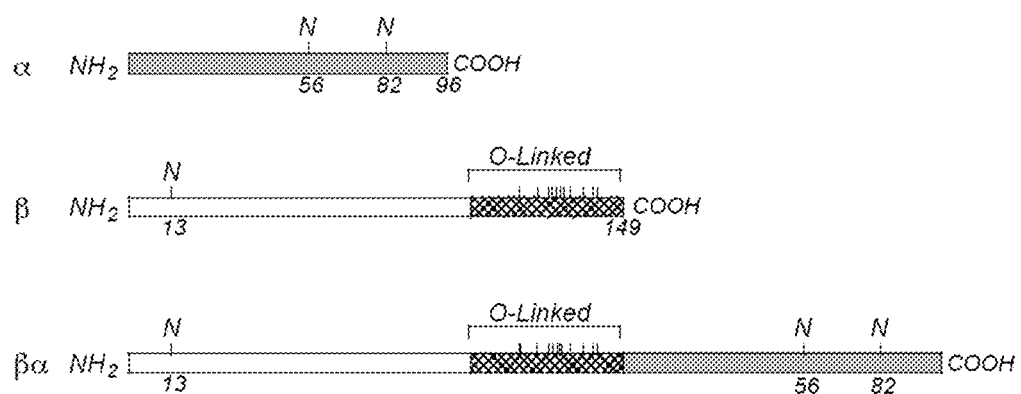
FIG. 2 is a schematic drawing of the eFSH analog of FIG. 1 where the alpha and beta subunits are linked together using an O-linked oligosaccharide (cross-hatched box) with the subunits arranged in tandem such that the beta subunit is N-terminal to the alpha subunit to form a single chain eFSH molecule.

As used herein, "breeding" refers to methods known in the art that pertain to making a female animal pregnant. Such methods include natural and artificial insemination. Breeding methods may include a waiting time after observation of behavioral estrus or after forcing estrus.

As used herein, "estrus" refers to the period during which an animal is most likely to become pregnant. As used herein, "forcing estrus" refers to methods known in the art for forcing heat. Forcing estrus can include waiting periods, as appropriate. As used herein, "behavioral estrus" refers to the behavioral demonstration that an animal is in heat, including showing standing heat.

"Mares" refer to female equines and "stallions" refer to male equines. As used herein, "cow" refers to female bovines, including heifers.

As used herein, "increasing reproductive activity" and "increasing reproductive efficiency" refers to increasing the likelihood that a female animal will become pregnant and ultimately produce a viable embryo or live offspring. This can be achieved by increasing the likelihood that an inseminated female animal becomes pregnant, increasing the likelihood that the pregnant animal produces one or more viable embryos, and/or by increasing the likelihood that pregnancy is maintained.

As used herein "ovulation synchronization" refers to a process whereby ovulation for a group of animals is forced, such that each animal is likely to ovulate within a 3-4-day window. As used herein, "estrus synchronization" refers to a process whereby estrus for a group of animals is forced, such that each animal is likely to be in estrus within about a 2-5-day window. As used herein, "estrus presynchronization" or "ovulation presynchronization" refers to a process whereby the estrus cycle, often for a group of animals, is blocked or forced into a particular stage of the cycle, so that estrus or ovulation synchronization procedures that are to be performed afterwards are more successful.

As used herein, "pregnant mammal" refers to a mammal that is currently pregnant and also includes a mammal that has been inseminated and may be pregnant or to a plurality of inseminated mammals, some of which are likely to be pregnant. As used herein, "insemination" refers to introducing semen by any method known in the art, including, but not limited to, natural and artificial insemination.

As used herein, "maintaining pregnancy" refers to increasing the likelihood that an animal which has been inseminated will test positive for pregnancy or will deliver a live offspring, or increasing likelihood that a plurality of animals that have been inseminated will test positive for pregnancy or will deliver a live offspring. By "pregnancy is maintained" it is meant that an animal remains pregnant at that time and that the embryo has not been lost.

As used herein, "effective amount" refers to an amount of an eFSH analog that is effective to produce the desired outcome.

As used herein, "administering" refers to any method of administering a therapeutic to an animal known in the art. Examples of administering include, but are not limited to, injecting the therapeutic subcutaneously, intramuscularly and intravenously.

As used herein, "therapeutic" refers to any drug, hormone, analog or compound used to treat, modify or improve a physiological condition. In the present invention, the physiological conditions are those related to reproduction, such as ovulation or maintaining pregnancy.

As used herein, "analog" refers to a compound which mimics the physiological effect of a natural compound. Analogs will typically be structurally similar to the natural compound but may have structural or chemical differences as a result of production methods or because the differences confer a beneficial activity to the analog. An eFSH analog is a composition having structural similarity and function to native eFSH.

As used herein, statements regarding purity such as "about 95% pure" refer to purity as measured by any method known in the art, including but not limited to protein electrophoresis. As used herein, statements regarding sequence homology for both amino acids and DNA, such as "95% or greater homology", refer to comparisons of sequences as understood and practiced in the art.

One embodiment of the invention encompasses a single chain recombinant eFSH analog having the amino acid sequence of SEQ ID NO 8, or an amino acid sequence having 90% or greater, preferably 95% or greater, homology to the amino acid sequence of SEQ ID NO 8. Another embodiment is a nucleic acid or a vector comprising a nucleic acid encoding a single chain amino acid having 90% or greater, preferably 95% or greater, homology to the amino acid sequence of SEQ ID NO 8. Another embodiment is a nucleic acid or a vector comprising a nucleic acid encoding a single chain amino acid having a first polypeptide with 90% or greater homology, preferably 95% or greater homology, to SEQ ID NO 5 and a second polypeptide with 90% or greater homology, preferably 95% or greater homology, to SEQ ID NO 6. Also encompassed are functional single chain recombinant eFSH analogs encoded by fragments of the nucleotide sequence provided in SEQ ID NO 8.

Example 1

Engineering and In Vitro Activity of Single-Chain Recombinant eFSH

To construct a single chain recombinant eFSH, the nucleotide sequence encoding the alpha subunit was inserted in frame at the 3' end of the eFSH beta subunit by using overlapping PCR mutagenesis. The carboxyl terminal peptide bearing the O-linked oligosaccharides was used as a linker (cross-hatched box) with the subunits arranged in tandem such that the beta subunit is N-terminal to the alpha subunit, as shown in FIG. 2. This method of engineering recombinant eFSH is similar to methods of engineering human chorionic gonadotropin (hCG) analogs (Sugahara et al. (1995) Proc Natl Acad Sci USA 1995; 92: 2041-2045; Narayan et al. (1995) "Functional expression of yoked human chorionic gonadotropin in baculovirus-infected insect cells," Mol Endocrinol 9: 1720-1726).

Figure 3:
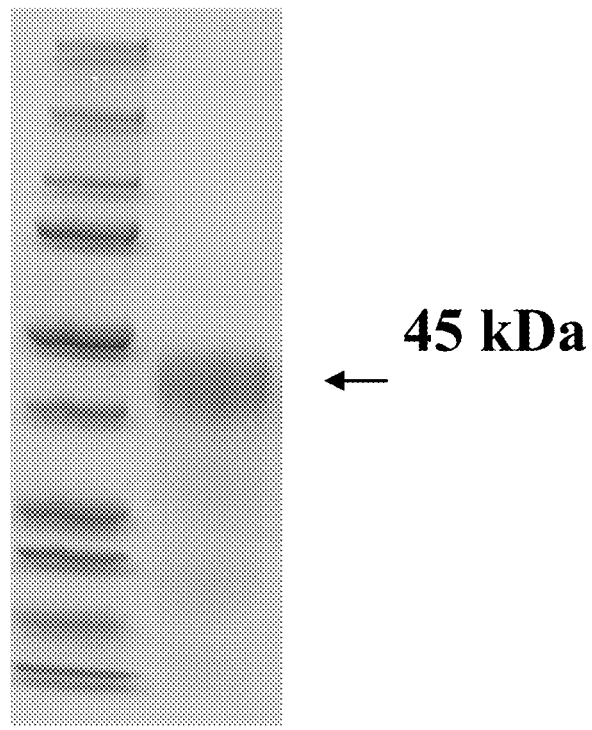
FIG. 3 illustrates an SDS-Page showing FSHβCTPα produced using methods of the present invention as a single 45 kDa spot.

The single chain construct was inserted into a vector and transfected into Chinese hamster ovary (CHO) cells, resulting in a single chain eFSH polypeptide, which was isolated and purified. An SDS-Page of FSHβCTPα, a single chain recombinant eFSH analog having the sequence of SEQ ID NO 8 and produced by this method, is shown in FIG. 3 as a predominant 45 kDa spot.

Figure 4:
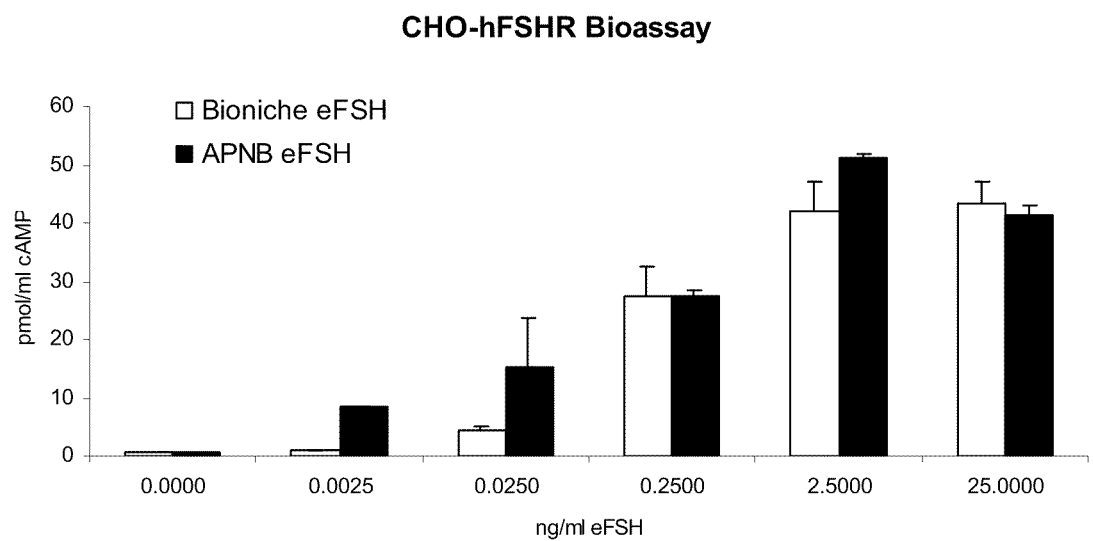
FIG. 4 is a graph comparing in vitro biological activity of FSHβCTPα (labeled in the figure as APNB eFSH) with native eFSH (purified pituitary extracts, Bioniche Animal Health) in a CHO-hFSHR assay.
Figure 5:
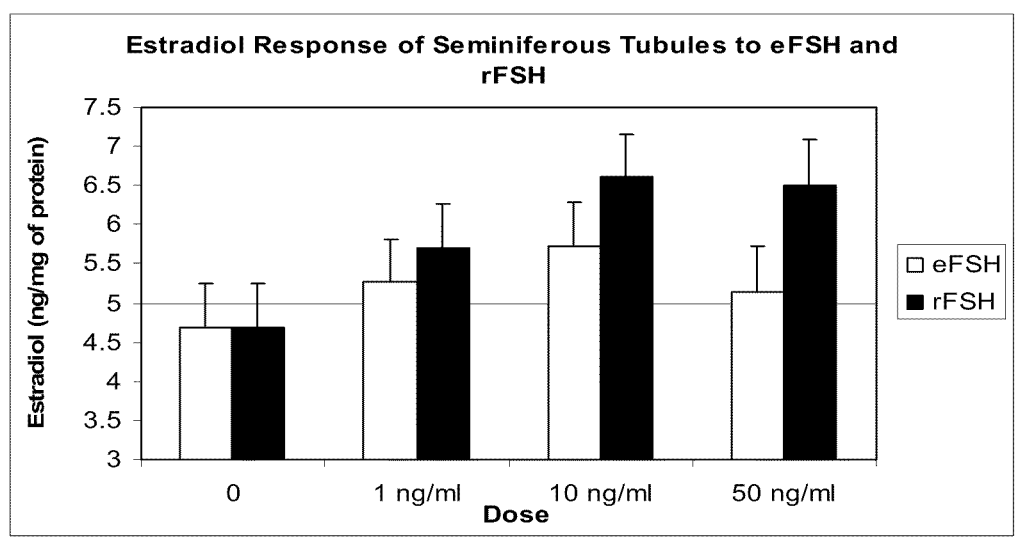
FIG. 5 is a graph comparing estradiol concentrations in spent media from equine seminiferous tubules incubated with native eFSH (from purified pituitary extracts) and FSH-βCTPα at various doses. A significant dose response was observed with the recombinant eFSH analog. At 50 ng/ml, the dose response of FSHβCTPα was greater than native eFSH.

The in vitro biological activity of FSHβCTPα was compared with native eFSH (purified pituitary extracts, Bioniche Animal Health) in a CHO-hFSHR assay. As shown in FIG. 4, FSHβCTPα (labeled APNB eFSH in the figure) has approximately equal or greater biological activity than the native eFSH, especially at lower doses (less than 0.25 ng/ml). Additionally, FIG. 5 compares estradiol concentrations in spent media from equine seminiferous tubules incubated with native eFSH and FSHβCTPα at various doses (n=9). A significant dose response was observed with FSHβCTPα and at 50 ng/ml, the dose response of FSHβCTPα was greater than native eFSH (p<0.05).

Example 2

Efficacy of Single Chain Recombinant eFSH in Cycling Mares

The in vivo efficacy of FSHβCTPα was further tested in cycling mares. Fifteen mares, from six to sixteen years of age, were housed in outdoor paddocks and given progesterone several days before ovulation, which is designated as day 0. The mares were then treated with progesterone and estradiol to suppress subsequent gonadotropin and ovarian activity. The estrus cycle of the mares resumed following withdrawal from the progesterone and estradiol treatment. The use of progesterone and estradiol to control estrus and ovulation is well known in the art (Loy et al. (1981) "Control of ovulation in cycling mares with ovarian steroids and prostaglandin;" Theriogenology 15:191-200; Varner et al. (1988) "Estrogens, oxytocin and ergot alkaloids—Uses in reproductive management of mares;" Proc. Am. Assoc. Equine. Pract., 219-241; Lofstedt, R. M. (1988) "Control of the estrous cycle of the mare;" The Veterinary Clinics of North America—Equine Practice, 189-190).

The fifteen mares were separated into three treatment groups, 5 mares in each group, with one group receiving 500 µg of the reFSH analog (FSHβCTPα), one group receiving 850 µg of the reFSH analog (FSHβCTPα), and one group receiving 1 ml of saline solution (control group). The recombinant eFSH analog or saline solution were administered twice daily (bi-daily or BID) on days 8-14 after ovulation. The animals were bred approximately 16-22 days after ovulation (approximately 2-8 days after the last recombinant eFSH administration) and checked for pregnancy. The effects of the treatments on follicular growth are shown in Table 1, and the effects on the number of follicles, ovulations and pregnancies are shown in Table 2.

TABLE 1

Follicular Growth Following Treatments

| | Treatment Groups | | |
|---|---|---|---|
| | 0.85 mg reFSH BID | 0.50 mg reFSH BID | Control |
| Mares (n) | 5 | 5 | 5 |
| No. follicles 20-29 mm at end of treatment (day 15) | 5.6 ± 1.24$^a$ | 4.8 ± 1.24$^a$ | 0.2 ± 0.20$^b$ |
| Time (days) to 35 mm follicle after withdrawal from P + E | 2.6 ± 0.51$^a$ | 3.3 ± 0.32$^a$ | 7.8 ± 0.51$^b$ |

$^{a,b}$Values within rows with different superscripts differ (p < 0.05).

TABLE 2

Number of Follicles, Ovulations and Pregnancies

|  | Treatment Groups | | |
|---|---|---|---|
|  | 0.85 mg reFSH BID | 0.50 mg reFSH BID | Control |
| Mares (n) | 5 | 5 | 5 |
| No. pre-ovulatory follicles (≥35 mm)[a] | 4.2 ± 0.58[b] | 3.4 ± 0.75[b] | 1.4 ± 0.24[c] |
| No. ovulations per mare (range) | 2.8 ± 0.51 (1-4) | 3.0 ± 0.93 (1-6) | 2.0 ± 0.32 (1-3) |
| No. non-ovulatory follicles (≥35 mm)[a] | 2.4 ± 1.12 | 2.0 ± 0.84 | 0.0 ± 0.00 |
| No. embryonic vesicles detected for each pregnant mare | 1, 2 | 1, 1, 5 | 1, 1, 1, 2 |

[a]Numbers from ultrasonic examination period 12 hours before first ovulation and 12 hours after last ovulation was detected.
[b,c]Values within rows with different superscripts differ ($p < 0.05$).

As shown in the above tables, the recombinant eFSH analog exhibited in vivo activity at both doses (850 μg and 500 μg) as shown by an increased number of follicles and ovulations per mare, and by the decreased time required to achieve 35 mm follicle size after withdrawal from the progesterone and estradiol treatment.

Example 3

Efficacy of Single Chain Recombinant eFSH on Superovulation

In this experiment, twenty normally cycling mares, three to thirteen years of age, were administered either native FSH (purified pituitary extract) or single chain recombinant eFSH. The mares were examined via transrectal ultrasonography at five days post ovulation. If the largest follicle was <25 mm in diameter, the mares were randomly assigned to one of four treatment groups and were administered an eFSH analog (FSHβCTPα):

Group A 12.5 mg Bioniche eFSH twice daily (positive control group, n=5)
Group B 500 μg recombinant eFSH (FSHβCTPα) twice daily (n=5)
Group C 850 μg recombinant eFSH (FSHβCTPα) once daily (n=5)
Group D 850 μg recombinant eFSH (FSHβCTPα) twice daily (n=5)

All mares received 10 mg dinoprost (prostaglandin) the evening of the second day of treatment and treatments continued until a cohort of follicles reached 32-35 mm in diameter. The mares received 1.5 mg recombinant eLH to induce ovulation about 38 hours after the last FSH treatment.

The mean days of FSH treatment were 6.6 (Group A), 7.2 (Group B), 8.0 (Group C), and 6.0 (Group D). The number of follicles>35 mm in diameter at the time of reLH administration were 3.2, 3.2, 3.0, and 4.2, respectively. The number of ovulations detected for the same groups were 3.8, 3.2, 5.4, and 3.4. The number of follicles>35 mm in diameter remaining at the time of ovulation for the same groups were 0.8, 1.6, 0.6, and 2.6. The results are summarized below in Table 3.

TABLE 3

| Treatment | Mare # | Days of Treatment | # Follicles >35 mm @ LH adminstration | # Ovulations | # Follicles >35 mm @ ovulation | # High quality embryos |
|---|---|---|---|---|---|---|
| 12.5 mg bid Bioniche | 408 | 6 | 2 | 3 | 0 |  |
|  | 625 | 5 | 2 | 3 | 2 |  |
|  | 579 | 10 | 2 | 2 | 0 |  |
|  | 418 | 6 | 3 | 3 | 2 |  |
|  | 419 | 6 | 7 | 8 | 0 |  |
|  |  | 6.6 | 3.2 | 3.8 | 0.8 |  |
| 0.5 mg bid reFSH | 503 | 6 | 3 | 3 | 0 |  |
|  | 525 | 6 | 4 | 5 | 0 |  |
|  | 106 | 8 | 3 | 3 | 3 |  |
|  | 507 | 8 | 3 | 3 | 2 |  |
|  | 502 | 8 | 3 | 2 | 3 |  |
|  |  | 7.2 | 3.2 | 3.2 | 1.6 |  |
| 0.85 sid reFSH | 424 | 9 | 4 | 6 | 0 |  |
|  | 644 | 8 | 4 | 5 | 0 |  |
|  | 850 | 5 | 2 | 6 | 1 |  |
|  | 645 | 10 | 3 | 4 | 2 |  |
|  | 97 | 8 | 2 | 6 | 0 |  |
|  |  | 8 | 3 | 5.4 | 0.6 |  |
| 0.85 bid reFSH | 128 | 4 | 3 | 3 | 0 |  |
|  | 66 | 5 | 4 | 4 | 1 |  |
|  | 459 | 7 | 3 | 5 | 0 |  |
|  | 454 | 5 | 6 | 4 | 6 | 4 |
|  | 152 | 9 | 5 | 1 | 6 | 7 |
|  |  | 6 | 4.2 | 3.4 | 2.6 |  |

These results indicate that reFSH has in vivo bioactivity in naturally cycling mares and may be a useful tool to stimulate follicular development/superovulation. All recombinant eFSH (FSHβCTPα) groups stimulated follicular development and produced multiple viable embryos. For all the parameters measured, values for the reFSH treatment groups were at least as effective as the positive control group (purified pituitary eFS.

The 850 μg reFSH dose given twice daily (bid) caused overstimulation of follicular development. Follicular stimulation continued in mares from this group for days after the majority of ovulations were detected. Viable embryos can be produced despite overstimulation, however, this effect was not noted to the same extent in the other reFSH groups. Accordingly, 500 μg administered twice daily may be preferable for practical applications. A hybrid protocol between two injections and a single injection daily (sid) is also likely to be effective.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known in the art including the compounds disclosed in the references disclosed herein are not intended to be included in the claim.

The invention claimed is:

1. A method of stimulating follicular development or superovulation in an ungulate comprising administering an effective amount of an equine follicle stimulating hormone (eFSH) analog to said ungulate, wherein said eFSH analog comprises a first polypeptide having at least 95% homology with SEQ ID NO 5, and a second polypeptide having at least 95% homology with SEQ ID NO 6, wherein said first and second polypeptides are covalently linked by an equine chorionic gonadotropin carboxy terminal peptide (CTP) having at least 90% homology with SEQ ID NO 7, wherein said effective amount is between approximately 200 µg and approximately 1.0 mg administered daily to said ungulate for approximately 4 to 9 days between day 6 to day 16 after ovulation.

2. The method of claim 1 wherein said ungulates are equine.

3. The method of claim 1 further comprising inseminating said ungulate between 2 to 8 days after administrating said eFSH analog.

4. The method of claim 1 wherein said eFSH analog has at least 95% homology with the full length sequence of SEQ ID NO 8.

5. The method of claim 1 wherein said effective amount is between approximately 500 µg and approximately 850 µg.

6. The method of claim 1 wherein a dose of the eFSH analog is administered daily to said ungulate for approximately 5 to 8 days in a single estrus cycle.

7. The method of claim 6 wherein a dose of the eFSH analog is administered twice daily to said ungulate for approximately 5 to 8 days in a single estrus cycle.

* * * * *

SEQUENCE LISTING

```
<160> NUMBER OF SEQ ID NOS: 8

<210> SEQ ID NO 1
<211> LENGTH: 291
<212> TYPE: DNA
<213> ORGANISM: Equus caballus

<400> SEQUENCE: 1
tcttttcctg atggagagtt tacaacgcaa gactgtcctg aatgcaagct aagggaaaac      60
aagtacttct tcaaactggg cgtcccgatt taccagtgta agggctgctg cttctccaga     120
gcgtacccca ctccagcaag gtccaggaag acaatgttgg tcccaaagaa catcacctca     180
gaatccacat gctgtgtggc caaagcattt atcagggtca cagtgatggg aaacatcaag     240
ttggagaacc acacccagtg ctattgcagc acttgctatc accacaagat t             291

<210> SEQ ID NO 2
<211> LENGTH: 387
<212> TYPE: DNA
<213> ORGANISM: Equus caballus
<220> FEATURE:
<221> NAME/KEY: misc_feature
<222> LOCATION: (78)..(78)
<223> OTHER INFORMATION: n is a, c, g, or t
```

```
<400> SEQUENCE: 2
atgaagtcag tccagttttg tttccttttc tgttgctgga aagcagtctg ctgcaatagc    60
tgtgagctga ccaacatnac catcgccgtg gagaaggagg aatgtggctt ctgcataagc   120
atcaacacca cctggtgtgc gggctactgc tacacccggg acctggtgta caaggaccca   180
gcccggccca acatccagaa acatgcacc ttcaaggagc tggtgtacga gacagtgaaa    240
gtgcctggct gtgctcacca cgcggactcc ctgtacacgt acccggtggc cactgcatgt   300
cactgtggca aatgtaacag cgacagcact gactgcaccg tgcgaggtct ggggcccagc   360
tactgctcct tcggtgacat gaaggaa                                       387

<210> SEQ ID NO 3
<211> LENGTH: 102
<212> TYPE: DNA
<213> ORGANISM: Equus caballus

<400> SEQUENCE: 3
tcctcttcct ctaaggatcc cccatcccaa cctctcacat ccacatccac cccaactcct    60
ggggccagca gacgttcctc tcacccccctc ccaataaaga ct                     102

<210> SEQ ID NO 4
<211> LENGTH: 783
<212> TYPE: DNA
<213> ORGANISM: Equus caballus
<220> FEATURE:
<221> NAME/KEY: misc_feature
<222> LOCATION: (78)..(78)
<223> OTHER INFORMATION: n is a, c, g, or t

<400> SEQUENCE: 4
atgaagtcag tccagttttg tttccttttc tgttgctgga aagcagtctg ctgcaatagc    60
tgtgagctga ccaacatnac catcgccgtg gagaaggagg aatgtggctt ctgcataagc   120
atcaacacca cctggtgtgc gggctactgc tacacccggg acctggtgta caaggaccca   180
gcccggccca acatccagaa acatgcacc ttcaaggagc tggtgtacga gacagtgaaa    240
gtgcctggct gtgctcacca cgcggactcc ctgtacacgt acccggtggc cactgcatgt   300
cactgtggca aatgtaacag cgacagcact gactgcaccg tgcgaggtct ggggcccagc   360
tactgctcct tcggtgacat gaaggaatcc tcttcctcta aggatccccc atcccaacct   420
ctcacatcca catccacccc aactcctggg gccagcagac gttcctctca cccctccca    480 ataaagactt cttttcctga tggagagttt acaacgcaag actgtcctga tgcaagcta   540 agggaaaaca agtacttctt caaactgggc gtcccgattt accagtgtaa gggctgctgc   600
ttctccagag cgtaccccac tccagcaagg tccaggaaga caatgttggt cccaaagaac   660
atcacctcag aatccacatg ctgtgtggcc aaagcattta tcagggtcac agtgatggga   720
aacatcaagt tggagaacca cacccagtgc tattgcagca cttgctatca ccacaagatt   780
taa                                                                 783

<210> SEQ ID NO 5
<211> LENGTH: 97
<212> TYPE: PRT
<213> ORGANISM: Equus caballus

<400> SEQUENCE: 5

Ser Phe Pro Asp Gly Glu Phe Thr Thr Gln Asp Cys Pro Glu Cys Lys
1               5                   10                  15
```

Leu Arg Glu Asn Lys Tyr Phe Phe Lys Leu Gly Val Pro Ile Tyr Gln
            20                  25                  30

Cys Lys Gly Cys Cys Phe Ser Arg Ala Tyr Pro Thr Pro Ala Arg Ser
        35                  40                  45

Arg Lys Thr Met Leu Val Pro Lys Asn Ile Thr Ser Glu Ser Thr Cys
    50                  55                  60

Cys Val Ala Lys Ala Phe Ile Arg Val Thr Val Met Gly Asn Ile Lys
65                  70                  75                  80

Leu Glu Asn His Thr Gln Cys Tyr Cys Ser Thr Cys Tyr His His Lys
                85                  90                  95

Ile

<210> SEQ ID NO 6
<211> LENGTH: 129
<212> TYPE: PRT
<213> ORGANISM: Equus caballus

<400> SEQUENCE: 6

Met Lys Ser Val Gln Phe Cys Phe Leu Phe Cys Cys Trp Lys Ala Val
1               5                   10                  15

Cys Cys Asn Ser Cys Glu Leu Thr Asn Thr Thr Ile Ala Val Glu Lys
            20                  25                  30

Glu Glu Cys Gly Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Asn
    50                  55                  60

Ile Gln Lys Thr Cys Thr Phe Lys Glu Leu Val Tyr Glu Thr Val Lys
65                  70                  75                  80

Val Pro Gly Cys Ala His His Ala Asp Ser Leu Tyr Thr Tyr Pro Val
                85                  90                  95

Ala Thr Ala Cys His Cys Gly Lys Cys Asn Ser Asp Ser Thr Asp Cys
            100                 105                 110

Thr Val Arg Gly Leu Gly Pro Ser Tyr Cys Ser Phe Gly Asp Met Lys
        115                 120                 125

Glu

<210> SEQ ID NO 7
<211> LENGTH: 34
<212> TYPE: PRT
<213> ORGANISM: Equus caballus

<400> SEQUENCE: 7

Ser Ser Ser Ser Lys Asp Pro Pro Gln Pro Leu Thr Ser Thr Thr Ser
1               5                   10                  15

Thr Pro Thr Pro Gly Ala Ser Arg Arg Ser Ser His Pro Leu Pro Ile
            20                  25                  30

Lys Thr

<210> SEQ ID NO 8
<211> LENGTH: 260
<212> TYPE: PRT
<213> ORGANISM: Equus caballus

<400> SEQUENCE: 8

Met Lys Ser Val Gln Phe Cys Phe Leu Phe Cys Cys Trp Lys Ala Val
1               5                   10                  15

Cys Cys Asn Ser Cys Glu Leu Thr Asn Thr Thr Ile Ala Val Glu Lys

-continued

```
                         20                  25                  30
        Glu Glu Cys Gly Phe Cys Ile Ser Ile Asn Thr Thr Trp Cys Ala Gly
                35                  40                  45

Tyr Cys Tyr Thr Arg Asp Leu Val Tyr Lys Asp Pro Ala Arg Pro Asn
                50                  55                  60

Ile Gln Lys Thr Cys Thr Phe Lys Glu Leu Val Tyr Glu Thr Val Lys
        65                  70                  75                  80

Val Pro Gly Cys Ala His His Ala Asp Ser Leu Tyr Thr Tyr Pro Val
                        85                  90                  95

Ala Thr Ala Cys His Cys Gly Lys Cys Asn Ser Asp Ser Thr Asp Cys
                    100                 105                 110

Thr Val Arg Gly Leu Gly Pro Ser Tyr Cys Ser Phe Gly Asp Met Lys
                115                 120                 125

Glu Ser Ser Ser Ser Lys Asp Pro Pro Ser Gln Pro Leu Thr Ser Thr
                130                 135                 140

Ser Thr Pro Thr Pro Gly Ala Ser Arg Arg Ser Ser His Pro Leu Pro
        145                 150                 155                 160

Ile Lys Thr Ser Phe Pro Asp Gly Glu Phe Thr Thr Gln Asp Cys Pro
                        165                 170                 175

Glu Cys Lys Leu Arg Glu Asn Lys Tyr Phe Phe Lys Leu Gly Val Pro
                    180                 185                 190

Ile Tyr Gln Cys Lys Gly Cys Cys Phe Ser Arg Ala Tyr Pro Thr Pro
                195                 200                 205

Ala Arg Ser Arg Lys Thr Met Leu Val Pro Lys Asn Ile Thr Ser Glu
                210                 215                 220

Ser Thr Cys Cys Val Ala Lys Ala Phe Ile Arg Val Thr Val Met Gly
        225                 230                 235                 240

Asn Ile Lys Leu Glu Asn His Thr Gln Cys Tyr Cys Ser Thr Cys Tyr
                        245                 250                 255

His His Lys Ile
                    260
```